United States Patent [19]
Rupp et al.

[11] Patent Number: 5,141,936
[45] Date of Patent: Aug. 25, 1992

[54] USE OF PYRIMIDO-(6,1-A)-ISOQUINOLIN-4-ONE DERIVATIVES AND MEDICINAL PREPARATIONS BASED ON THESE COMPOUNDS

[75] Inventors: Richard H. Rupp, Königstein/Taunus, Fed. Rep. of Germany; Bansi Lal, Bombay, India

[73] Assignee: Hoechst Aktiengesellschaft, Frankfurt am Main, Fed. Rep. of Germany

[21] Appl. No.: 353,280

[22] Filed: May 17, 1989

[30] Foreign Application Priority Data

May 19, 1988 [DE] Fed. Rep. of Germany ....... 3816995

[51] Int. Cl.⁵ ................. A61K 31/505; A61K 31/535; A61K 31/41; A61K 31/47
[52] U.S. Cl. ............................ 514/227.8; 514/233.2; 514/255; 514/267
[58] Field of Search ................. 514/227.8, 233.2, 255, 514/267, 83, 86; 424/70

[56] References Cited

U.S. PATENT DOCUMENTS

| | | | |
|---|---|---|---|
| 4,482,556 | 11/1984 | Lal et al. | 544/115 |
| 4,598,148 | 7/1986 | Lal et al. | 544/252 |
| 4,828,837 | 5/1989 | Uster et al. | 424/449 |

FOREIGN PATENT DOCUMENTS

| | | |
|---|---|---|
| 0211268 | 2/1987 | European Pat. Off. |
| 2720085 | 11/1978 | Fed. Rep. of Germany . |
| 2801289 | 5/1979 | Fed. Rep. of Germany . |
| 3601739A1 | 7/1987 | Fed. Rep. of Germany . |

OTHER PUBLICATIONS

V. C. Weiss et al., Arch Dermatol, 1984, 120, 457.
Bansi Lal et al., J. Med. Chem., 1984, 27, 1470–1480.

*Primary Examiner*—Robert T. Bond
*Assistant Examiner*—E. C. Ward
*Attorney, Agent, or Firm*—Finnegan, Henderson, Farabow, Garrett and Dunner

[57] ABSTRACT

Pyrimido-(6,1-a)-isoquinolin-4-one derivatives of the formula

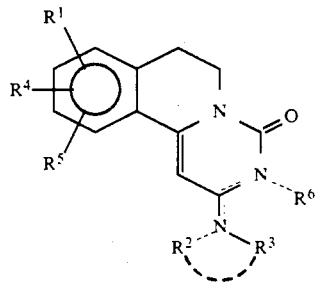

in which the substituents $R^1$–$R^6$ have the meanings mentioned, are suitable for the prevention of hair loss and for strengthening hair growth.

2 Claims, No Drawings

USE OF PYRIMIDO-(6,1-A)-ISOQUINOLIN-4-ONE DERIVATIVES AND MEDICINAL PREPARATIONS BASED ON THESE COMPOUNDS

DESCRIPTION

The present invention relates to the use of pyrimido-(6,1-a-)-isoquinolin-4-one derivatives and medicinal preparations based on these compounds.

Alopecia or baldness results from the loss of hair. Dermatologists differentiate between various types of hair loss (for example alopecia areata, alopecia totalis or androgenetic alopecia), by far the most widespread being known as androgenetic alopecia or "male pattern alopecia or baldness". Although this type of hair loss is largely limited to men, it is not unknown in women. The alopecia or baldness condition is the result of a linking of factors: (1) transformation of hairs from the terminal to the vellus state, (2) large number of telogenic hairs, of which some have been rubbed off and (3) loss of hair roots. Very little is known about the causes of male pattern baldness, although it is suspected that this could have a genetic or hormonal origin. At the present point in time, attempts are being made to cure male pattern alopecia either on the one hand by non-medicinal approaches such as hair transplantation, massage under ultraviolet irradiation, psychiatric treatment and exercise therapy or on the other hand by medicinal treatment. Concerning the non-medicinal solution approaches to the problem, it is known that they may either be generally ineffective or, in the case of transplantation, too expensive, time-consuming and impracticable. In the case of medicinal therapy, many types of therapeutic medicaments which extend from vitamins to hormones or diphenylhydantoin and streptomycin have been tested out, and only recently has an indication of a modest success been given there. The conditions which give cause for the modest hope of growing hair again by their external use on the scalp of a sufferer from male baldness includes the use (1) of a microemulsion cream containing an estradiol or oxandrolone, or (2) organic silicon or (3) minoxidil.

Surprisingly, it has now been found that pyrimido-(6,1-a)-isoquinolin-4-ones of the general formula I are remarkably effective agents for the transformation of vellus to terminal hair, for the acceleration of terminal hair growth and for stopping the loss of hair, by which they represent possible agents for the treatment, stopping and reversal of alopecia (for example alopecia totalis, alopecia areata), in particular male pattern alopecia (androgenetic alopecia). Pyrimido-(6,1-a)-isoquinolin-4-ones have already been described in DE-OS 2,720,085 and DE-OS 2,801,289 where, however, only their effectiveness for the control of hypertonia, bronchospasms and allergies are mentioned.

The invention therefore relates to the use of pyrimido-(6,1-a)-isoquinolin-4-one derivatives of the formula I

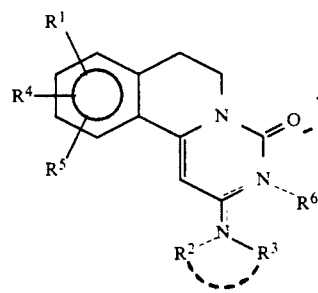

in which $R^1$, $R^4$ and $R^5$, which may be identical or different, may be hydrogen, hydroxyl, lower alkoxy, dialkylphosphinylalkoxy, acyloxy or halogen, where two adjacent groups together may denote a methylenedioxy or ethylenedioxy group, and $R^2$ and $R^3$, which may be identical or different, may be hydrogen, hydroxyl, lower alkoxy, amino, alkylamino, dialkylamino, arylamino, alkyl, amino or alkyl substituted by a 5- or 6-membered carbon ring which may contain up to 3 heteroatoms from the group comprising N, 0 or S, cycloalkyl, hydroxyalkyl, alkoxyalkyl, dialkoxyalkyl, haloalkyl, dialkylaminoalkyl, aralkyl, acyl and, optionally substituted, aryl, where aryl is in each case taken to mean an aromatic hydrocarbon having up to 10 carbon atoms, and $R^2$ denotes an electron pair if $R^6$ denotes one of the radicals indicated below and $R^2$ and $R^3$ together with the nitrogen atom to which they are bonded may denote a part of an optionally substituted nitrogen heterocycle which may contain a further nitrogen atom or an oxygen atom, and $R^6$ stands for hydrogen, alkyl, cycloalkyl, hydroxyalkyl, alkoxyalkyl, dialkoxyalkyl, haloalkyl, dialkylaminoalkyl, aralkyl, heterocyclic-substituted alkyl, dialkylphosphinylalkyl, acyl and optionally substituted aryl, and also stands for an electron pair if $R^2$ denotes one of the radicals indicated above, and their acid salts and quaternary ammonium salts, for strengthening hair growth and/or for preventing hair loss.

If at least one of the two radicals $R^2$ and $R^3$ stands for a hydrogen atom, the above definition of the pyrimido-(6,1-a)-isoquinolin-4-one derivatives also includes the isomers Ib corresponding to the following formula, either obtained by complete isomerization of the compounds of the formula Ia or being in equilibrium with the compounds of the formula Ia.

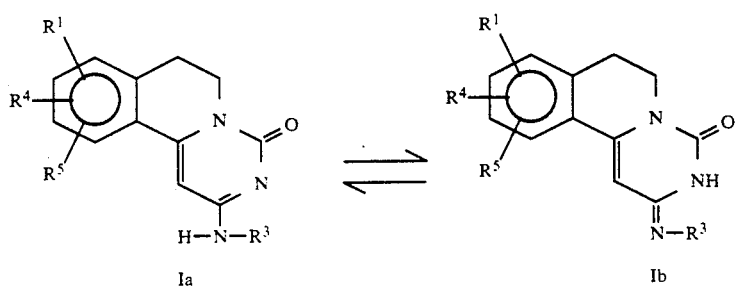

Ia          Ib

The definition of the pyrimido-(6,1-a)-isoquinolin-4-one derivatives also includes the Ic isomer of the following formula, in which $R^1$, $R^3$, $R^4$, $R^5$ and $R^6$ have the above meaning.

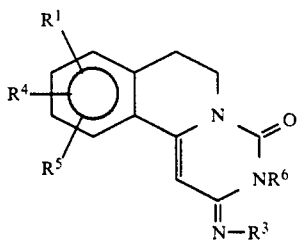

Ic

Suitable lower alkoxy groups for $R^1$, $R^2$, $R^3$, $R^4$ and $R^5$ are, for example, those having up to 3 carbon atoms.

If $R^1$, $R^4$ or $R^5$ stand for an acyloxy radical, those radicals may be mentioned as suitable in which the acyl group denotes a straight-chain or branched alkanoyl group having 1-6 carbon atoms, for example the acetyl group, or an aroyl group, in particular the benzoyl group containing a phenyl ring which is optionally monosubstituted to trisubstituted by halogen, nitro, hydroxyl, alkoxy and alkyl groups, where the two last groups have at most 3 carbon atoms.

If $R^1$, $R^4$ or $R^5$ denotes a halogen atom, chlorine, for example, may be mentioned as a suitable radical.

If $R^1$, $R^4$, $R^5$ or $R^6$ stand for a dialkylphosphinylalkoxy radical, suitable radicals are those in which the alkyl and alkoxy groups have at most 3 carbon atoms each, for example the dimethylphosphinylmethoxy radical.

Particularly suitable alkylamino or dialkylamino radicals for $R^2$ or $R^3$ are those having alkyl groups having at most 3 carbon atoms, for example methylamino or dimethylamino groups.

Suitable arylamino radicals for $R^2$ or $R^3$ are phenylamino radicals having alkyl groups having at most 3 carbon atoms which are optionally monosubstituted or polysubstituted by halogen, for example chlorine, for example methyl or a phenyl radical substituted by the nitro group. A suitable amino group substituted by a nitrogen-containing heterocycle for $R^2$ or $R^3$ is, for example, the n-morpholinoamino radical.

Suitable alkyl radicals for $R^2$, $R^3$ or $R^6$ are those having at most 6 carbon atoms, such as, for example, methyl, ethyl, n-propyl, isopropyl, butyl, isobutyl, sec-butyl or tert-butyl.

Suitable cycloalkyl radicals for $R^2$, $R^3$ or $R^6$ which may be mentioned are those having at most 6 carbon atoms, such as, for example, cyclohexyl.

As a substituted alkyl radical for $R^2$, $R^3$ or $R^6$, a radical having up to 6 carbon atoms may be employed, which may be substituted with one or two hydroxyl or alkoxy groups, where the alkoxy groups at most each have 3 carbon atoms, furthermore halogen, for example chlorine, amino or dialkylamino, where the alkyl groups have at most 4 carbon atoms, and also dialkylphosphinoalkyl, for example dimethylphosphinylmethyl.

Examples of aralkyl radicals for $R^2$, $R^3$ or $R^6$ are those having at most 8 carbon atoms, in which the aryl radical may be monosubstituted or polysubstituted, in particular monosubstituted, disubstituted or trisubstituted with the substituents indicated above for $R^1$.

Suitable heterocyclic alkyl radicals for $R^2$, $R^3$ or $R^6$ are, for example, furfuryl or tetrahydrofurfuryl groups.

Suitable aryl radicals for $R^2$, $R^3$ or $R^6$ are, for example, alkyl and alkoxy groups having at most 3 carbon atoms which are optionally monosubstituted or polysubstituted, in particular monosubstituted, disubstituted or trisubstituted, by halogen atoms, for example fluorine, chlorine or bromine atoms, for example methyl, ethyl, methoxy and ethoxy groups, haloalkyl groups, for example trifluoromethyl groups, amino or phenyl radicals substituted by hydroxyl groups, where the hydrogen atoms in the hydroxyl groups may be replaced by an alkali metal, for example sodium.

Suitable radicals of nitrogen-containing heterocycles are, for example, the pyrrolidino, piperidino, morpholino or piperazino radical, which may be substituted by alkyl, alkoxycarbonyl, aryl or a nitrogen heterocycle, where alkyl, alkoxy, aryl or nitrogen heterocycle have the above meaning.

Examples of suitable acyl radicals for $R^2$, $R^3$ or $R^6$ are straight-chain or branched alkanoyl radicals having 1-6 carbon atoms, such as acetyl, or aroyl, such as benzoyl, where the phenyl radical may be monosubstituted or polysubstituted by the substituents mentioned above for $R^2$, $R^3$ and $R^5$, if these denote an aryl radical.

Salts of the pyrimido-(6,1-a)-isoquinolin-4-one derivatives according to the present invention which may be mentioned are, for example, those of inorganic or organic acids, for example hydrochlorides, hydrobromides, sulfates, phosphates, acetates, oxalates, tartrates, citrates, maleates or fumarates.

Suitable quaternary ammonium salts of the pyrimido-(6,1-a)-isoquinolin-4-one derivatives of the invention are, for example, those of salts derived from alkyl halides such as methyl iodide.

Preferred substituents are the following:

$R^1$ or $R^4$ is alkoxy, $R^5$ is hydrogen, $R^2$ is $C_{1-6}$-alkyl or phenyl which is optionally monosubstituted to trisubstituted by substituents of the above-mentioned type, and $R^3$ and $R^5$ are hydrogen, $C_{1-6}$-alkyl, cycloalkyl, substituted alkyl, aralkyl, heterocyclic alkyl, substituted aryl and $C_{1-6}$-alkanoyl.

Particularly preferred is the use according to the invention of 9,10-dimethoxy-2-tert-butylamino-6,7-dihydro-4H-pyrimido-(6,1-a)-isoquinolin-4-one hydrochloride, 9,10-dimethoxy-2-(2,4,6-trimethylanilino)-6,7-dihydro-4H-pyrimido-(6,1-a)-isoquinolin-4-one hydrochloride dihydrate, 9,10-dimethoxy-3-methyl-2-mesitylimino-2,3,6,7-tetrahydro-4H-pyrimido-(6,1-a)-isoquinolin-4-one hydrochloride, 9,10-dimethoxy-2-(N-methyl-2,4,6-trimethylanilino)-6,7-dihydro-4H-pyrimido-(6,1-a)-isoquinolin-4-one hydrochloride, 9,10-dimethoxy-3-isopropyl-2-mesitylimino-2,3,6,7-tetrahydro-4H-pyrimido-(6,1-a)-isoquinolin-4-one hydrochloride, 9,10-dimethoxy-2-(N-isopropyl-2,4,6-trimethylanilino)-6,7-dihydro-4H-pyrimido-(6,1-a)-isoquinolin-4-one hydrochloride, 9,10-dimethoxy-3-ethyl-2-mesitylimino-2,3,6,7-tetrahydro-4H-pyrimido-(6,1-a)-isoquinolin-4-one hydrochloride, 9,10-dimethoxy-2-(N-ethyl-2,4,6-trimethylanilino)-6,7-dihydro-4H-pyrimido-(6,1-a)-isoquinolin-4-one hydrochloride, 9,10-dimethoxy-3-acetyl-2-mesitylimino-2,3,6,7-tetrahydro-4H-pyrimido-(6,1-a)-isoquinolin-4-one, 9,10-dimethoxy-2-sec-butylamino-6,7-dihydro-4H-pyrimido-(6,1-a)-isoquinolin-4-one hydrochloride, 9,10-dimethoxy-2-(2,6-dimethylanilino)-6,7-dihydro-4H-pyrimido-(6,1-a)-isoquinolin-4-one, 9,10-dimethoxy-2-(2,4-dimethylanilino)-6,7-dihydro-4H-pyrimido-(6,1-a)-isoquinolin-4-one, 9,10-dimethoxy-2-(2-chloroanilino)-6,7-dihydro-4H-pyrimido-(6,1-a)-isoquinolin-4-one hydrochloride monohydrate, 9,10-dimethoxy-2-(2,4,6-trimethylanilino)-6,7-dihydro-4H-pyrimido-(6,1-a)-isoquinolin-4-one hydrochloride dihydrate, 9,10-dimethoxy-3-acetyl-2-mesitylimino-2,3,6,7-tetrahydro-4H-pyrimido-(6,1-a)-isoquinolin-4-one and 9,10-dimethoxy-2-(N-acetyl-2,4,6-trimethylanilino)-6,7-dihydro-4H-pyrimido-(6,1-a)-isoquinolin-4-one.

Particularly preferred is the use according to the invention of 9,10-dimethoxy-2-mesitylimino-3-methyl-2,3,6,7-tetrahydro-4H-pyrimido-(6,1-a)-isoquinolin-4-one hydrochloride (trequinsin).

The preparation of the compounds utilizable according to the invention is, for example, described in DE-OS 2,720,085 and DE-OS 2,801,289, to which express reference is made.

The use according to the invention of the compounds of the formula I can in principle take place in all mammals; it has particular significance for man. A compound of the formula I is preferably administered externally to the skin of the mammal.

The medicinal preparations according to the invention include those which are suitable for external and local treatment. A compound according to the invention is used together with a pharmaceutically acceptable excipient which is suitable for external treatment for the preparation of conventional medicinal preparations such as, for example, solutions, suspensions, emulsions, pastes, ointments, gels, creams, lotions, powders, soaps, surfactant-containing cleaning preparations, oils and sprays. Any customary excipients and auxiliaries are added to the preparation in addition to the active compound.

Preferable auxiliaries come from the group comprising the preservatives, antioxidants, stabilizers, solubilizers, vitamins, colorants and odor enhancers.

Ointments, pastes, creams and gels may contain the customary excipients, for example animal and vegetable fats, waxes, paraffins, starch, tragacanth, cellulose derivatives, polyethylene glycols, silicones, bentonites, silicic acid, talc and zinc oxide or mixtures of these substances in addition to the active compound(s).

Powders and sprays may contain the customary excipients, for example lactose, talc, silicic acid, aluminum hydroxide, calcium silicate and polyamide powder or mixtures of these substances in addition to the active compound(s). Sprays may additionally contain the customary propellants, for example chlorofluorohydrocarbons, propane/butane or dimethyl ether.

Solutions and emulsions may contain the customary excipients such as solvents, solubilizers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, groundnut oil, maize germ oil, olive oil, castor oil and sesame oil, glycerol fatty acid esters, polyethylene glycols and fatty acid esters of sorbitan or mixtures of these substances in addition to the active compound(s).

Suspensions may contain the customary excipients such as liquid diluents, for example water, ethanol, propylene glycol, suspending agents, for example ethoxylated isostearyl alcohols, polyoxyethylene sorbitol and sorbitan esters, microcrystalline cellulose, aluminum metahydroxide, bentonite, agar-agar and tragacanth or mixtures of these substances in addition to the active compound(s).

Soaps may contain the customary excipients such as, for example, alkali metal salts of fatty acids, salts of fatty half esters, fatty acid protein hydrolysates, isethionates, lanolin, fatty alcohols, vegetable oils, plant extracts, glycerol, sugar or mixtures of these substances in addition to the active compound(s).

Surfactant-containing cleaning products may contain the customary excipients such as, for example, salts of fatty alcohol sulfates, fatty alcohol ether sulfates, sulfosuccinic acid half esters, fatty acid protein hydrolysates, isethionates, imidazolinium derivatives, methyl laurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters or mixtures of these substances in addition to the active compound(s).

Facial and body oils may contain the customary excipients, such as, for example, synthetic oils such as fatty acid esters, fatty alcohols, silicone oils, natural oils such as vegetable oils and oily plant extracts, paraffin oils, lanolin oil or mixtures of these substances in addition to the active compound(s).

The physiologically effective amount of pharmacologically acceptable combinations is applied to the skin as often as necessary. The concentration used of one of the compounds according to the invention is in the range from 0.1% to 20% of the pharmaceutical preparation. The preferred concentration range is 0.5-6%. The number of daily applications to the skin depends on the concentration of the active constituents applied.

The invention is intended to be illustrated in more detail by the following example.

EXAMPLE 1

1,000 cm$^3$ of a 3% strength aqueous solution containing 9,10-dimethoxy-2-mesitylimino-3-methyl-2,3,6,7-tetrahydro-4H-pyrimido-(6,1-a)-isoquinolin-4-one hydrochloride is prepared from the following constituents in the amounts indicated.

| | |
|---|---|
| dimethoxy-2-mesitylimino-3-methyl-2,3,6,7-tetrahydro-4H-pyrimido-(6,1-a)-isoquinolin-4-one hydrochloride (trequinsin) | 30 g |
| Propylene glycol | 250 g |
| Deionized water to | 1,000 g |

The constituents are dissolved in water and the resulting solution is sterilized by filtration. The solution is aseptically drawn off into sterile containers. The solutions are also prepared in a similar manner using dimethylacetamide or ethyl alcohol instead of or in combination with propylene glycol.

The abovementioned solutions can be used for accelerating terminal hair growth, for activating the transformation of vellus into growth as terminal hair and for stopping the loss of hair externally on the skin of the mammal.

Detection of hair growth-promoting effect of trequinsin

Male and female rabbits having a weight of 500–700 g and an age of 5–6 weeks were used for the experiments. The animals were kept with the mother during the entire experiment.

The rear part of the experimental animals was shaved in four sites (two on each side) using electric hair clippers. Each animal had 4 shaved sites of 3 cm$^2$ each. 18 hours after shaving, 0.2 ml of trequinsin solution (see Example 1) having a varying trequinsin concentration and also solvent as a blank sample were placed on each shaved site and massaged in for about 60 sec. The application was repeated daily and at the end of each week in each case 10 hairs were pulled out from each site and their length was determined. The statistical significance was determined by means of the "Student T Test". Trequinsin solutions having a content of 2, 3 and 4 percent of active compound were used.

The summary of the results is shown in Table 1. Trequinsin in a concentration of 2% led to an acceleration of hair growth of 26% after 1 week, 42% after 2 weeks and 40% after 3 weeks. Similar data resulted for trequinsin in a concentration of 3%; the acceleration of hair growth here was 47% after 2 weeks and 100% after 3 weeks. Using the sample containing 4% trequinsin gave only an insignificant acceleration of hair growth.

TABLE 1

Hair growth in mm in rabbits under the influence of treatment with trequinsin solutions

| Treatment period in weeks | Hair growth in mm in rabbits under the influence of treatment with trequinsin solutions | | | |
|---|---|---|---|---|
| | Solvent | Trequinsin solution | | |
| | | 2.0% | 3.0% | 4.0% |
| 1 | 10.16 + 0.34 | 12.85 + 0.43** | 9.93 + 0.57* | 11.46 + 0.73* |
| 2 | 15.09 + 0.69 | 21.53 + 0.71** | 22.0 + 0.61** | 16.46 + 1.67* |
| 3 | 14.48 + 0.93 | 20.26 + 1.24** | 29.0 + 0.44** | 12.96 + 1.03* |

*not significant
**$P < 0.001$

We claim:

1. A method for accelerating hair growth comprising administering externally to the skin of a mammal a medicinal preparation containing a medicinally acceptable carrier and an effective amount in the range from 0.1% to 3.0% of a compound selected from the group consisting of:

9,10-dimethoxy-2-mesitylimino-3-methyl-3,4,6,7-tetrahydro-2H-pyrimido-(6,1-a)-isoquinolin-4-one hydrochloride, 9,10-dimethoxy-2-tert-butylamino-6,7-dihydro-4H-pyrimido-(6,1-a)-isoquinolin-4-one hydrochloride, 9,10-dimethoxy-2-(2,4,6-trimethylanilino)-6,7-dihydro-4H-pyrimido-(6,1-a)-isoquinolin-4-one hydrochloride dihydrate, 9,10-dimethoxy-3-methyl-2-mesitylimino-2,3,6,7-tetrahydro-4H-pyrimido-(6,1-a)-isoquinolin-4-one hydrochloride, 9,10-dimethoxy-2-(N-methyl-2,4,6-trimethylanilino-6,7-dihydro-4H-pyrimido-(6,1-a)-isoquinolin-4-one hydrochloride, 9,10-dimethoxy-3-isopropyl-2-mesitylimino-2,3,6,7-tetrahydro-4H-pyrimido-(6,1-a)-isoquinolin-4-one hydrochloride, 9-10-dimethoxy-2-(N-isopropyl-2,4,6-trimethylanilino)-6,7-dihydro-4H-pyrimido-(6,1-a)-isoquinolin-4-one hydrochloride, 9-10-dimethoxy-3-ethyl-2-mesitylimino-2,3,6,7-tetrahydro-4H-pyrimido-(6,1-a)-isoquinolin-4-one hydrochloride, 9,10-dimethoxy-2-(N-ethyl-2,4,6-trimethylanilino)-6,7-dihydro-4H-pyrimido-(6,1-a)-isoquinolin-4-one hydrochloride, 9,10-dimethoxy-3-acetyl-2-mesitylimino-2,3,6,7-tetrahydro-4H-pyrimido-(6,1-a)-isoquinolin-4-one and 9,10-dimethoxy-2-(N-acetyl-2,4,6-trimethylanilino)-6,7-dihydro-4H-pyrimido-(6,1-a)-isoquinolin-4-one.

2. The method of claim 1 where the compound is 9,10-dimethoxy-2-mesitylimino-3-methyl-3,4,6,7-tetrahydro-2H-pyrimido-(6,1-a)-isoquinolin-4-one hydrochloride.

* * * * *